United States Patent

Samuelsson et al.

[11] 3,949,088
[45] Apr. 6, 1976

[54] SUBSTITUTED PHENOXY PROPANOL AMINES USED FOR TREATING CARDIOVASCULAR DISEASES

[76] Inventors: Benny Roger Samuelsson, Tubavagen 1B, S-435 00 Molnlycke; Gert Christer Strandlund, Ranunkelgatan 7D, S-431 32 Molndal, both of Sweden

[22] Filed: Apr. 16, 1974

[21] Appl. No.: 461,288

[30] Foreign Application Priority Data
Apr. 18, 1973 Sweden.............................. 7305502

[52] U.S. Cl.......... 424/324; 260/465 D; 260/465 E; 260/471 C; 260/559 A; 260/562 R; 260/570.7; 424/301
[51] Int. Cl.²........................................ A61K 31/165
[58] Field of Search..................................... 424/324

[56] References Cited
UNITED STATES PATENTS

| | | | |
|---|---|---|---|
| 3,644,469 | 2/1972 | Koppe et al. ................... | 424/304 X |
| 3,836,671 | 9/1974 | Barrett et al. ................... | 424/330 X |
| 3,857,873 | 12/1974 | Schuenoer et al. ............. | 424/330 X |

*Primary Examiner*—Leonard Schenkman
*Attorney, Agent, or Firm*—Brumbaugh, Graves, Donohue & Raymond

[57] ABSTRACT

A new amine of the formula

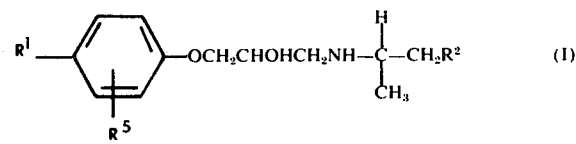 (I)

wherein $R^1$ is loweralkylthio loweralkyl, loweralkoxy loweralkoxy, loweralkylcarbonylamino loweralkyl or loweralkoxycarbonylamino loweralkyl, $R^2$ is benzyl, phenoxyloweralkyl, cyano or the group

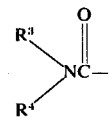

wherein $R^3$ and $R^4$ are hydrogen or loweralkyl and $R^5$ is hydrogen, halogen, loweralkyl, loweralkenyl, loweralkinyl, loweralkoxymethyl, loweralkoxy, loweralkenyloxy or loweralkinyloxy, a pharmaceutical preparation containing the same and a method for treating cardiovascular diseases.

28 Claims, No Drawings

SUBSTITUTED PHENOXY PROPANOL AMINES USED FOR TREATING CARDIOVASCULAR DISEASES

The present invention relates to amines of formula I

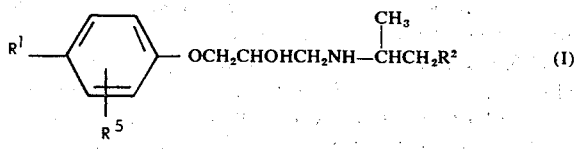

wherein R' is loweralkylthio loweralkyl, loweralkoxy loweralkoxy, loweralkoxycarbonylamino loweralkyl, or loweralkylcarbonylamino loweralkyl, and $R^5$ may be a substituent and $R^2$ is benzyl, phenoxyloweralkyl, cyano or the group

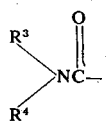

and whereby $R^3$ and $R^4$ are hydrogen or loweralkyl, as well as a process for their preparation.

The term "lower" residue will be understood to be especially such a residue having up to 4 carbon atoms.

Loweralkylthio loweralkyl $R^1$ has in its loweralkyl part of the loweralkylthio part up to 4 carbon atoms. Thus, loweralkyl is e.g. iso-or n-propyl, straight or branched butyl bound in any position, suitably ethyl and preferably methyl. The loweralkyl part carrying the loweralkylthio part has up to 4 carbon atoms and is e.g. branched or preferably straight chain lower alkyl having preferably at least 1 carbon atom in the alkyl chain, especially having 2 to 4 carbon atoms in the alkyl chain. Loweralkylthio loweralkyl $R^1$ is e.g. methylthiomethyl, 2-methylthioethyl, 2-ethylthioethyl, 3-ethylthio n-propyl, 4-methylthio n-butyl, and preferably 3-methylthio n-propyl.

Loweralkylcarbonylamino loweralkyl $R^1$ has in the loweralkyl part of the loweralkylcarbonylamino part up to 4 carbon atoms. The loweralkyl part carrying the loweralkylcarbonylamino part has up to 4 carbon atoms and is e.g. branched or preferably straight chain lower alkyl having at least 1 carbon atom in the alkyl chain, suitably 2 to 4 carbon atoms in the alkyl chain. Loweralkylcarbonylamino loweralkyl $R^1$ is e.g. methylcarbonylamino methyl, 2-ethylcarbonylaminoethyl, 3-ethylcarbonylamino n-propyl, 4-methylcarbonylamino n-butyl and preferably 2-methylcarbonylaminoethyl or 3-methylcarbonylamino n-propyl.

Loweralkoxy loweralkoxy $R^1$ has in the loweralkyl part of the loweralkoxy part up to 4 carbon atoms. The loweralkoxy part carrying the loweralkoxy part has up to 4 carbon atoms and is e.g. branched or preferably straight chain loweralkoxy having preferably 2 carbon atoms in the alkyl chain. Loweralkoxy loweralkoxy $R^1$ is e.g. methoxyethoxy, 3-ethoxy n-propoxy, 3-methoxy, n-butoxy and preferably 2-methoxyethoxy or 3-methoxy n-propoxy.

Loweralkoxycarbonylamino loweralkyl $R^1$ has in the loweralkyl part of the loweralkoxy part up to 4 carbon atoms. The loweralkyl part carrying the loweralkoxycarbonylamino part has up to 4 carbon atoms and is e.g. branched or preferably straight chain loweralkyl. Loweralkoxycarbonylamino loweralkyl $R^1$ is e.g. ethoxycarbonylaminomethyl, 2-ethoxycarbonylaminoethyl, 3-ethoxycarbonylamino n-propyl, 4-methoxycarbonylamino n-butyl and preferably methoxycarbonylaminomethyl, 2-methoxycarbonylaminoethyl or 3-methoxycarbonylamino n-propyl.

Optionally substituted phenylene Ph is e.g. optionally substituted paraphenylene. Suitable substituents are halogen, trifluormethyl, loweralkyl, loweralkenyl, loweralkinyl, loweralkoxymethyl, loweralkoxy, loweralkenyloxy and loweralkinyloxy. If a substituent is present on the phenylene, it is present, in the case of a paraphenylene, preferably in ortho position to the aminopropanoloxy side chain.

Halogen is e.g. fluoro, bromo and preferably chloro.

Loweralkyl $R^5$ has preferably up to 4 carbon atoms, as iso- and n-propyl, straight or branched chain and in any position bonded butyl, pentyl, hexyl and heptyl, suitably ethyl and preferably methyl.

Loweralkenyl $R^5$ has for example up to 4 carbon atoms, as vinyl, 2-methylvinyl, methallyl and preferably allyl.

Loweralkinyl $R^5$ has for example up to 4 carbon atoms, as 1-propinyl, 2-propinyl and ethinyl.

Loweralkoxymethyl $R^5$ has in its loweralkyl part of the loweralkoxy part up to 4 carbon atoms, as ethyl, iso- or n-propyl, and especially methyl and is e.g. ethoxymethyl and preferably methoxymethyl.

Loweralkoxy $R^5$ has up to 4 carbon atoms, and is e.g. ethoxy, iso- or n-propoxy, and preferably methoxy.

Loweralkenyloxy $R^5$ has e.g. up to 4 carbon atoms, preferably 3 or 4 carbon atoms as methallyloxy, or preferably allyloxy.

Loweralkinyloxy $R^5$ has e.g. up to 4 carbon atoms, preferably 3 or 4 carbon atoms such as 2-propinyloxy.

The following compounds may be mentioned illustrating compounds containing groups $R^5$ 1-(4-(2-methoxyethoxy)-2-allyloxyphenoxy)-2-hydroxy-3-(2-N-methylcarbamoyl-1-methylethyl)-aminopropane;

1-(4-(2-acetamidoethyl)-2-chloro-phenoxy)-2-hydroxy-3-(2-carbamoyl-1-methylethyl)-aminopropane;

1-(4-(2-methoxycarbonylamino ethyl)-2-bromo-phenoxy)-2-hydroxy-3-(2-N-methylcarbamoyl-1-methylethyl)-aminopropane;

1-(4-(2-methoxyethoxy)-2-fluorophenoxy)-2-hydroxy-3-(2-N,N-dimethylcarbamoyl-1-methylethyl)-aminopropane;

1-(4-(2-methylthioethyl)-2-methoxy-phenoxy)-2-hydroxy-3-(2-benzyl-1-methylethyl)-aminopropane;

1-(4-(2-methylthioethoxy)-2-allylphenoxy)-2-hydroxy-3-(2-carbamoyl-1-methylethyl)-aminopropane.

Phenoxyloweralkyl $R^2$ has in the loweralkyl part up to 4 carbon atoms. Thus phenoxyloweralkyl $R^2$ is e.g. phenoxymethyl, phenoxyethyl, phenoxy n-propyl, or phenoxy n-butyl, preferably phenoxymethyl and phenoxyethyl.

Monoloweralkylcarbamoyl $R^2$ and diloweralkylcarbamoyl $R^2$ have in each loweralkyl part up to 4 carbon atoms. Thus monoloweralkylcarbamoyl R is methylcarbamoyl, ethylcarbamoyl, n-propylcarbamoyl, preferably methylcarbamoyl, ethylcarbamoyl or isopropylcarbamoyl or tert-butylcarbamoyl. Diloweralkylcarbamoyl $R^2$ is dimethylcarbamoyl, diethylcarbamoyl, di-n-propylcarbamoyl, or di-n-butylcarbamoyl, preferably di-isopropylcarbamoyl or ditert-butylcarbamoyl.

Compounds where $R^2$ is phenoxyalkyl may be mentioned, including 1-(4-(2-methoxyethoxy)-phenoxy)-2-hydroxy-3-(3-phenoxy-1-methylpropyl)-aminopropane and 1-(4-(2-acetamidoethyl) -2-allylphenoxy)-2-hydroxy-3-(4-phenoxy-1-methylbutyl)-aminopropane.

The new compounds have valuable pharmacological properties. Thus, they block cardiac β-receptors, which is shown in the determination of the antagonism of tachycardia after an intravenous injection of 0.5 μg/kg of d/l-isoproterenol sulphate on an anaesthetized cat with an intravenous dose of 0.002 to 2 mg/kg. Thus, they block the vascular β-receptors, which is shown in the determination of the antagonism of vasodilation after an intravenous injection of 0.5 μg/kg of d/l-isoproterenol sulphate on an anaesthetized cat with an intravenous dose of 3 mg/kg or more. Thus, they block the cardiac β-receptors, which is shown in the determination of tachycardia after the addition of 0.005 μg/ml of d/l-isoproterenol sulphate to an isolated guinea-pig heart in vitro at a concentration of 0.02 to 2 mg/ml.

The new compounds can be used as cardioselective antagonists of adrenergic β-receptor-stimulators e.g. in the treatment of arrhythmias and angina pectoris. One may also use them as valuable intermediates in the preparation of other useful compounds, especially pharmaceutically active compounds.

Outstanding amines are those according to formula I

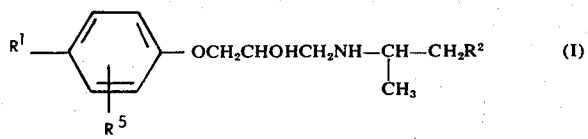

wherein $R^1$ and $R^2$ have the above given meanings and $R^5$ is hydrogen, halogen, loweralkyl, loweralkenyl, loweralkinyl, loweralkoxymethyl, loweralkoxy, loweralkenyloxy, or loweralkinyloxy.

Especially amines Ia of formula I will be mentioned, wherein $R^1$ is loweralkylthio loweralkyl, loweralklcarbonylamino loweralkyl or loweralkoxycarbonylamino loweralkyl, $R^2$ is benzyl, phenoxy loweralkyl, cyano or the group

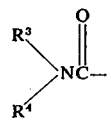

and $R^3$, $R^4$ and $R^5$ have the above given meanings.

Of the amines Ia those will be mentioned wherein $R^1$ is loweralkylthioloweralkyl, loweralkylcarbonylamino loweralkyl, or loweralkoxycarbonylamino loweralkyl, $R^2$ is carbamoyl, N-loweralkylcarbamoyl, N,N-diloweralkylcarbamoylbenzyl or cyano, and $R^5$ is hydrogen, halogen, loweralkyl, loweralkenyl, loweralkoxymethyl, loweralkoxy or loweralkenyloxy.

Of the amines Ia those will especially be mentioned wherein $R^1$ is 2-methylthioethyl, 3-methylthio-n-propyl, methylcarbonylaminomethyl, 2-(methylcarbonylamino)ethyl, methoxycarbonylaminomethyl or 2-(methoxycarbonylamino)ethyl, $R^2$ is carbamoyl, N-methylcarbamoyl, N,N-dimethylcarbamoyl or cyano and $R^5$ is hydrogen, fluoro, chloro, methyl, allyl, methoxymethyl, methoxy or allyloxy.

Of the amines Ia those will preferably be mentioned wherein $R^1$ is 2-methylthioethyl, 3-methylthio n-propyl, acetamidoethyl, methoxycarbonylaminomethyl, or 2-(methoxycarbonylamino) ethyl, $R^2$ is carbamoyl, N-methylcarbamoyl, N,N-dimethylcarbamoyl, benzyl or cyano, and $R^5$ is hydrogen.

Named are especially 1-(2-carbamoyl-1-methylethyl)amino-3-[4'-,2-acetamidoethyl)-phenoxy]-propanol-2, 1-(2-cyano-1-methylethyl)-amino-3-[4'-(2-methylthioethyl)-phenoxy]-propanol-2, 1-(2-benzyl-1-methylethyl)amino-3-[4'-(2-methoxycarbonylaminoethyl)-phenoxy]-propanol-2 and 1-[2-(N-methyl)carbamoyl-1-methylethyl]amino-3-[4'-(2-acetamidoethyl)-phenoxy]-propanol-2.

Especially amines Ib of the formula I will be mentioned, wherein $R^1$ is loweralkoxy loweralkoxy, $R^2$ is benzyl, phenoxyloweralkyl, cyano or the group

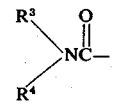

and $R^3$, $R^4$ and $R^5$ have the above given meanings.

Of the amines Ib those will be mentioned wherein $R^1$ is loweralkoxyloweralkoxy, $R^2$ is benzyl, phenoxyloweralkyl, carbamoyl, N-loweralkylcarbamoyl, N,N-diloweralkylcarbamoyl, or cyano and $R^5$ is hydrogen, halogen, loweralky, loweralkenyl, loweralkoxymethyl, loweralkoxy or loweralkenyloxy.

Of the amines Ib those will especially be mentioned, wherein $R^1$ is 2-ethoxyethoxy, 2-methoxyethoxy, or 3-methoxy-n-propoxy, $R^2$ is benzyl, phenoxymethyl, carbamoyl, N-methylcarbamoyl, N,N-dimethylcarbamoyl, or cyano and $R^5$ is hydrogen, fluoro, chloro, methyl, allyl, methoxymethyl, methoxy or allyloxy.

Of the amines Ib those will preferably be mentioned, wherein $R^1$ is 2-methoxyethoxy or 3-methoxy n-propoxy, $R^2$ is carbamoyl, N-methylcarbamoyl, or N,N-dimethylcarbamoyl, and $R^5$ is hydrogen.

Named is especially 1-[(2-methylcarbamoyl-1-methyl) ethyl]amino-3-[4'-(2-methoxyethoxy)phenoxy]-propanol-2 and 1-(2-carbamoyl-1-methylethyl)amino-3-[4'-(2-methoxyethoxy)phenoxy]-propanol-2.

The new compounds are obtained according to methods known per se. Thus a compound of formula III

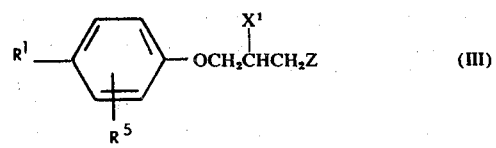

wherein R¹ and R⁵ have the meanings given above, X¹ is a hydroxy group and Z is a reactive, esterified hydroxy group, or X¹ and Z together form an epoxy group, is reacted with an amino of the formula

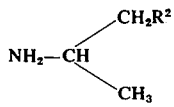

wherein R² has the meaning given above.

A reactive, esterified hydroxy group is particularly a hydroxy group esterified with a strong, inorganic or organic acid, preferably a hydrohalogen acid, and as hydrochloric acid, hydrobromic acid, or hydroiodic acid, further sulphuric acid or a strong organic sulphonic acid such as a strong aromatic sulphonic acid, e.g. benzenesulphonic acid, 4-bromobenzenesulphonic acid or 4-toluenesulphonic acid. Thus, Z is preferably chloro, bromo or iodo.

This reaction is carried out in a known way. When using a reactive ester as a starting material, the preparation takes place preferably in the presence of a basic condensing agent and/or with an excess of an amine. Suitable basic condensing agents are e.g. alkali metal hydroxides such as sodium or potassium hydroxide, alkali metal carbonates such as potassium carbonate and alkali metal alcoholates such as sodium methylate, potassium ethylate and potassium tert.-butylate.

Further, a compound of formula IV

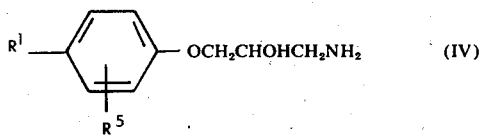

wherein R¹ and R⁵ have the same meanings as given above, is reacted with a compound of the formula

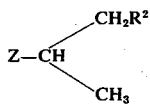

wherein R² and Z have the meanings given above.

This reaction is carried out in a known way, preferably in the presence of a basic condensing agent and/or an excess of an amine. Suitable basic condensing agents are e.g. alkaline alcoholates, preferably sodium or potassium alcoholate, or also alkaline carbonates such as sodium or potassium carbonate.

Further, a compound of formula V

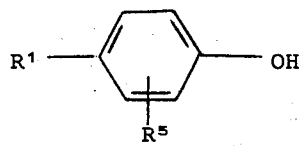

wherein R¹ and R⁵ have the same meanings as given above is reacted with a compound of formula VI

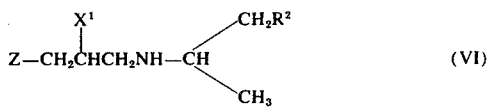

wherein Z, X¹ and R² have the meanings given above.

This reaction is carried out in a known way. In those cases where reactive esters are used as starting material, the compound of formula V may suitably be used in the form of its metal phenolate such as alkalimetal phenolate, preferably sodium phenolate, or one works in the presence of an acid binding agent, preferably a condensing agent, which can form a salt of the compound of formula V, such as an alkalimetal alcoholate.

Further, one may, from a compound of formula I above, wherein R¹, R² and R⁵ have the same meanings as above and in which the nitrogen atom of the amino group and/or the hydroxy group has attached thereto a splitable residue, split off this residue.

Such splitable residues are especially those which are splitable by solvolysis, reduction, pyrolysis or fermentation.

Residues splitable by solvolysis are preferably residues splitable by hydrolysis or ammonolysis.

Residues splitable by means of hydrolysis are e.g. an acyl residue, which, when present are functionally varied carboxy groups, e.g. oxycarbonyl residues, such as alkoxycarbonyl residues e.g. tert.-butoxycarbonyl residue, or ethoxycarbonyl residue, aralkoxycarbonyl residues such as phenylloweralkoxycarbonyl residues, e.g. a carbobenzyloxy residue, halogencarbonyl residue, e.g. a chlorocarbonyl residue, further arylsulphonyl residues such as toluenesulphonyl or bromobenzenesulphonyl residues and possibly as halogenated, such as fluorinated loweralkanoyl residues such as formyl-, acetyl- or trifluoroacetyl residue or a benzyl residue or cyano group or silyl residue such as a trimethylsilyl residue.

Of the above mentioned residues present at the hydroxy groups, which residues are splitable by hydrolysis preferably the oxycarbonyl residues and the loweralkanoyl residues or the benzoyl residues are used.

Besides the above mentioned, also double-bounded residues, which are splitable at the amino group by hydrolysis may be used, e.g. an alkylidene or benzylidene residue or a phosphorylidene group such as a triphenylphosphorylidene group, whereby the nitrogen atom then takes a positive charge.

Other residues splitable at the hydroxy group and the amino group by hydrolysis are divalent residues such as substituted methylene. As substituents on the methylene residues, any organic residue may be used, so that it does not matter in the hydrolysis which compound is the substituent on the methylene residue. As methylene substituents e.g. aliphatic or aromatic residues such as alkyl as mentioned above, aryl e.g. phenyl or pyridyl may be used. The hydrolysis may be carried out in any usual way, suitably in a basic or preferably in an acid medium.

Compounds having residues which are splitable by hydrolysis also include the compounds according to formula VII

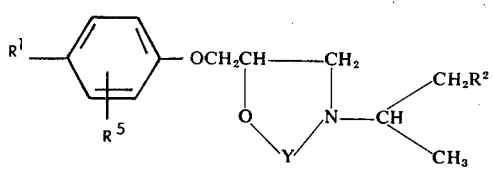

(VII)

wherein $R^1$, $R^2$ and $R^5$ have the same meanings as given above and Y is a carbonyl or thiocarbonyl residue.

The hydrolysis is carried out in an analogous way, e.g. in the presence of a hydrolysing agent, or e.g. in the presence of acidic agents such as dilute mineral acids, e.g. sulphuric acid or hydrohalogen acid, or in the presence of basic agents such as alkalimetal hydroxides, e.g. sodium hydroxide. Oxycarbonyl residues, aryl sulphonyl residues and cyano groups may in a suitable way be split off by means of acidic agents as by means of a hydrohalogen acid, suitably hydrobromic acid. Preferably, the splitting may take place using diluted hydrobromic acid, possibly in a mixture with acetic acid. Cyano groups are preferably split off by means of hydrobromic acid at an elevated temperature, as in boiling hydrobromic acid, according to the "bromocyano method" (v. Braun). Further, for example, a tert-butoxycarbonyl residue may be split off under anhydrous conditions by treatment with a suitable acid, such as trifluoroacetic acid. Acidic agents are preferably used in the hydrolysis of compounds of formula VII.

Residues splitable by ammonolysis are especially the halogencarbonyl residues, such as the chlorocarbonyl residue. The ammonolysis may be carried out in a known way, e.g. by means of an amine containing at least one hydrogen atom bound to the nitrogen atom, as a mono- or di-loweralkylamine, e.g. methylamine or dimethylamine, or especially ammonia, preferably at an elevated temperature. Instead of ammonia one may use an agent which gives ammonia such as hexamethylenetetraamine.

Residues splitable by means of a reduction are e.g. an α-arylalkyl residue, such as a benzyl residue or an α-aralkoxycarbonyl residue such as a benzyloxycarbonyl residue, which in a known way may be split off by hydrogenolysis, especially by catalytically activated hydrogen, as by hydrogen in the presence of hydrogenating catalysts, e.g. Raney-nickel. Other residues splitable by means of hydrogenolysis are 2-halogenalkoxycarbonyl residues such as 2,2,2-tri-chloroethoxycarbonyl residues or 2-iodoethoxy- or 2,2,2-tribromoethoxycarbonyl residues, which may be split off in a known way, suitably by metallic reduction (so called nascent hydrogen). Nascent hydrogen may be obtained by the action of metal or metal alloys, such as amalgam, on compounds which give hydrogen such as carboxyacids, alcohols or water, wherein especially zinc or zinc-alloys together with acetic acid may be used. Hydrogenolysis of 2-halogenalkoxycarbonyl residues may further take place using chromium or chromium (II) compounds such as chromium (II) chloride or chromium (II) acetate.

A suitable residue splitable by reduction may also be an arylsulphonyl group such as a toluenesulphonyl group, which in a usual way may be split off by reduction using nascent hydrogen, e.g. by means of an alkalimetal, such as lithium or sodium in liquid ammonia, and suitably may be split off from a nitrogen atom. In carrying out the reduction, one has to take care that other reducing groups are not affected.

Residues splitable by means of pyrolysis, especially residues splitable from the nitrogen atom, are in suitable cases substituted, or unsubstituted carbamoyl groups, Suitable substituents are e.g. loweralkyl or arylloweralkyl such as methyl or benzyl or aryl, such as phenyl. The pyrolysis is carried out in a known way, wherein one may have to take care of other thermally susceptible groups.

Residues splitable by means of fermentation, especially residues splitable from the nitrogen atom are in suitable cases substituted, however, on occasion unsubstituted carbamoyl groups. Suitable substituents are e.g. loweralkyl or arylloweralkyl, such as methyl or benzyl, or aryl e.g. phenyl. The fermentation is carried out in a usual way, e.g. by means of the enzyme urease or soybean extract at about 20°C or a slightly elevated temperature.

Further, a Schiff's base of formula VIII or IX

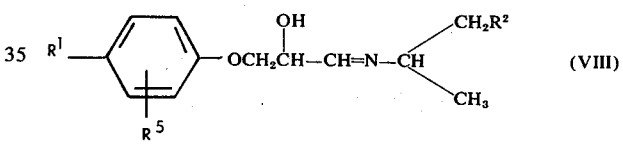

(VIII)

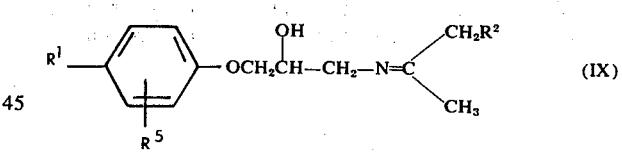

(IX)

or a cyclic tautomer corresponding to formula IX or formula X

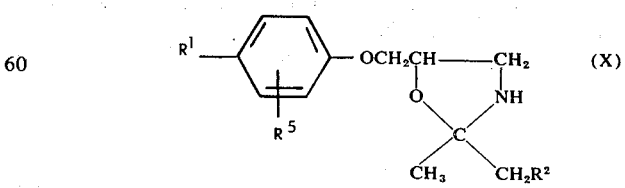

(X)

can be reduced, wherein $R^1$, $R^2$ and $R^5$ have the same meaning as given above. The compounds of formula VIII and IX may exist together, too.

This reduction is carried out in a known manner, e.g. using a di-lightmetalhydride, such as sodium boronhydride, lithiumaluminiumhydride, using a hydride such as Boran with formic acid, or by catalytic hydrogenation, as with hydrogen in the presence of Raney-nickel. In the reduction one has to take care that other groups are not affected.

Further, in a compound of formula XI

wherein $R^2$ and $R^5$ have the same meanings as given above, and wherein $X^2$ is a residue which is able to be transformed to a residue $R^1$ having the same meaning as given above, one transforms $X^2$ to $R^1$.

A residue $X^2$ able to be transformed into $R^1$ is e.g. a residue transformable to a loweralkylcarbonylamino loweralkyl, loweralkoxycarbonylamino loweralkyl or loweralkylthio loweralkyl residue $R^1$, such as a $Z^1$-loweralky residue. A compound XI having such a residue $Z^1$-loweralkyl as $X^2$ can be reacted in a known way with a compound loweralky-$Z^2$ wherein one of $Z^1$ and $Z^2$ is a hydroxy group or mercapto group and the other Z has the meaning given above. Thus, one can react either a compound of formula XII

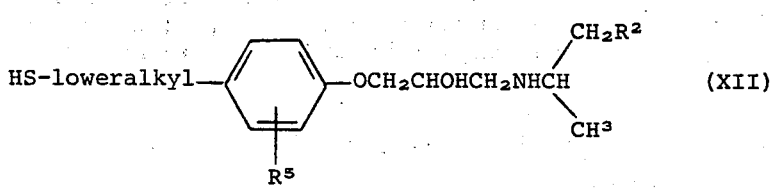

with a compound loweralkyl-$Z^2$ or a compound of formula XIII

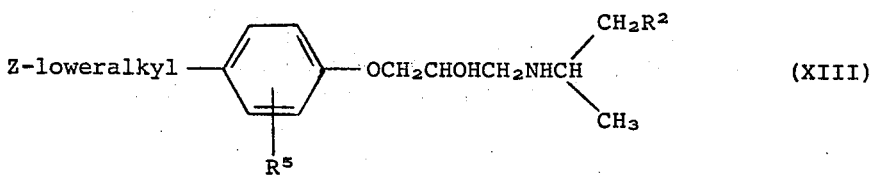

with a compound loweralkyl-SH wherein $R^2$, $R^5$ and Z have the meanings given above.

The reaction is carried out in a known way, e.g. as has been mentioned for the reaction of a compound of formula III with an amine $$NH_2-\overset{H}{\underset{CH_3}{C}}-CH_2R^2$$

A residue $X^2$ transformable into $R^1$ is e.g. a residue $X^2$ transformable into a loweralkylcarbonylamino loweralkyl, or loweralkyloxycarbonylamino loweralkyl residue $R^1$, such as a residue Z-loweralkyl.

The compound XI with such a residue Z-loweralkyl as $X^2$ can be reacted in a known way with a loweralkylcarbonylamine or a loweralkyoxycarbonylamine, wherein Z has the meaning given above.

Thus, one can react a compound of formula XIV

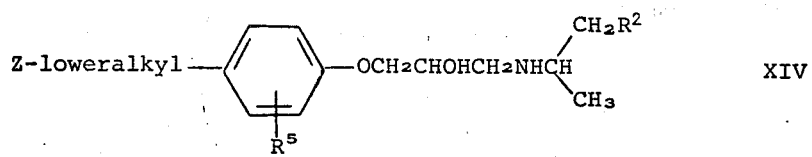

with a compound loweralkyl-CO-$NH_2$ or a compound loweralkoxy-CO-$NH_2$ wherein $R^2$, $R^5$ and Z have the meanings given above. The reaction is carried out in known way, e.g. as has been mentioned for the reaction of a compound of formula III with an amine $$NH_2-\overset{H}{\underset{CH_3}{C}}-CH_2R^2$$

A residue $X^2$ transformable into $R^1$ is e.g. a residue $X^2$ transformable into a loweralkylcarbonylamino loweralkyl or a loweralkoxycarbonylamino loweralkyl residue $R^1$ such as a residue $H_2N$-loweralkyl.

A compound XI having such a residue $H_2N$-loweralkyl can in a known way be reacted with a loweralkylcarbonylchloride or a loweralkoxycarbonylchloride.

Thus, one can react a compound of the formula XVIII

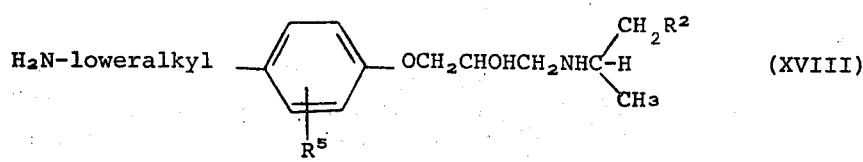

with a loweralkylcarbonylchloride or a loweralkoxycarbonylchloride, wherein $R^2$ and $R^5$ have the meanings given above. The reaction is carried out in a known way e.g. as has been mentioned for the reaction of a compound of formula III with an amine

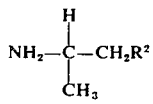

A residue transformable into $R^1$ is e.g. a residue $X^2$ transformable into a residue loweralkoxycarbonylamino loweralkyl $R^1$ as a residue $Z^1$-CO-NH-loweralkyl.

A compound XI having such a residue $Z^1$-CO-NH-loweralkyl as $X^2$ can in a known way be reacted with a compound loweralkyl-$Z^2$, wherein $Z^1$ and $Z^2$ have the meanings given above.

Thus one can react a compound of the formula XIX

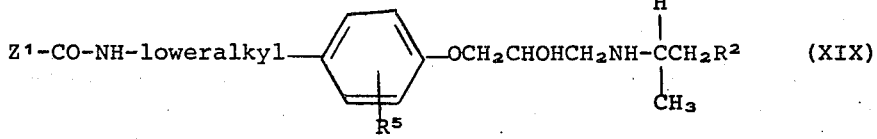

with a compound loweralkyl-$Z^2$, wherein $R^2$, $R^5$, $Z^1$ and $Z^2$ have the meanings given above.

A residue $X^2$ transformable into $R^1$ is e.g. a residue $X^2$ transformable into a residue loweralkoxy loweralkoxy $R^1$ such as a residue $Z^1$-loweralkyl-O- or a hydroxy group.

A compound XI having such a residue $Z^1$-loweralkyl-O as $X^2$ can in a known way be reacted with a compound loweralkyl-$Z^2$, wherein one of the residues $Z^1$ and $Z^2$ is hydroxy and the other Z has the meaning given above.

Thus, one can react either a compound of the formula XV

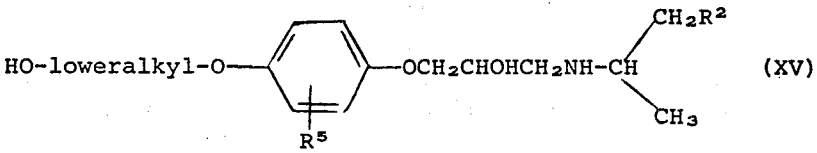

with a compound loweralkyl-Z, or a compound of formula XVI

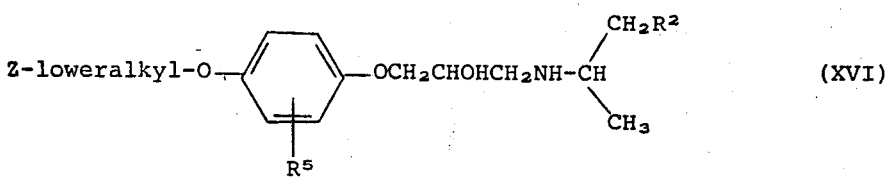

with a compound loweralky-OH, wherein $R^2$, $R^5$ and Z have the meanings given above. The reaction is carried out in a known way e.g. as has been mentioned for the reaction of a compound of the formula III with an amine

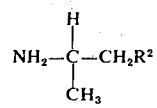

A compound of formula XI having a hydroxy group as a residue $X^2$ can be reacted in a known way with a compound, loweralkoxy loweralkyl-Z wherein Z has the same meaning as above.

Thus, one can react a compound of formula XVII

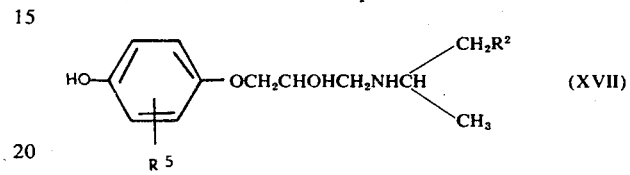

with a compound loweralkoxy loweralkyl-Z, wherein $R^5$ and Z have the meanings given above. The reaction is carried out in a known way, e.g. as the reaction of a compound of formula III with an amine.

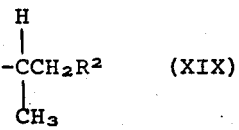

Further in a compound corresponding to formula I which compound carries an oxo group at a carbon atom bound to a nitrogen atom, this oxo group may be reduced to two hydrogen atoms. In such cases the residue $R^1$ is preferably not a loweralkylcarbonylamino loweralkyl or a loweralkoxycarbonylamino loweralkyl and the residue $R^2$ is not a carbamoyl or a mono or diloweralkylcarbamoyl.

Said compounds are e.g. such of the formula XVIII

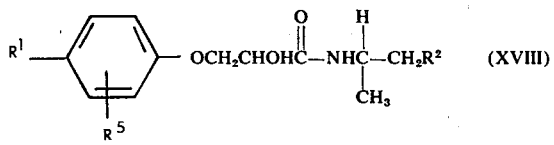

wherein $R^1$, $R^2$ and $R^5$ have the meaning given above.

The reduction can be carried out according to the above described manner using complex metal hydrides, e.g. lithiumaluminiumhydride or di-isobutylaluminumhydride. Suitably the reaction takes place in an inert solvent such as an ether, e.g. diethylether or tetrahydrofuran.

In a known way the substituents may be varied from the compounds obtained within the definition of the end product as well as the compounds obtained may be introduced, split off or transformed into other end products in a known way.

Thus, it is possible to hydrogenate catalytically C—C double-bonds or C—C triple bonds to C—C single bonds by means of hydrogen in the presence of a hydrogenation catalyst, e.g. platinum, palladium or nickel, such as Raney-nickel. One should take care that other reduceable groups are not reduced.

In compounds obtaind containing a C—C triple bond this may further be transformed into a C—C double bond and, if desired, be hydrogenated stereospecifically into a C—C-cis or C—C-trans double bond. The hydrogenation of a C—C triple bond to a C—C double bond may, for example, be carried out using 1 mole of hydrogen in the presence of a less active hydrogenation catalyst such as iron or palladium, e.g. Raney-iron or palladium with barium sulphate, preferably at an elevated temperature. The hydrogenation to a C—C-cis double bond may take place e.g. between 1 mole of hydrogen and a deactivated catalyst, such as palladium on active carbon and in the presence of quinoline, palladium on calcium carbonate in the presence of lead salts or Raney-nickel. The hydrogenation to a C-C-trans double bond may take place by means of sodium in liquid ammonia, wherein with regard to other reduceable groups short reaction times are used and no excess of the reducing agent is used, possibly an ammonium halogenide, such as ammonium chloride, being added as a catalyst.

In the reduction mentioned above one has to see to it that no further reduceable groups are reduced. In the reduction using Raney-nickel and hydrogen one has to consider especially a possibly present halogen atom bonded to the aromatic ring, so that it is not replaced by hydrogen. Furthermore, in all reductions, especially catalytic hydrogenations, one has to consider any thioether group present. Preferably sulphur-resistent catalysts are used and, in actual cases, the volume of hydrogen to be absorbed in calculated and when the calculated amount is absorbed in the hydrogenation the reduction is finished.

The above-mentioned reactions may possibly be carried out simultaneously or one after the other in any sequence.

The above-mentioned reactions are carried out in a manner known per se in the presence or absence of diluting, condensing and/or catalytical agents at a low room or an elevated temperature, possibly being carried out in a closed vessel.

Depending on the process conditions and the starting material the end product is obtained either in free form or in the form of its acid addition salt, which is included in the scope of the invention. Thus, for example, basic, neutral or mixed salts may be obtained as well as hemiamino, sesqui- or polyhydrates. The acid addition salts of the new compounds may in a manner known per se be transformed into free compounds using e.g. basic agents such as alkalies or ion exchangers. On the other hand, the free bases obtained may form salts with organic or inorganic acids. In the preparation of acid addition salts preferably such acids are used which form suitable therapeutically acceptable salts. Such acids are e.g. hydrohalogen acids, sulphuric acid, phosphoric acid, nitric acid, perchloric acid, aliphatic, alicyclic, aromatic or heterocyclic carboxy or sulphonic acids, such as formic, acetic, propionic, succinic, glycolic, lactic, malic, tartaric, citric, ascorbic, maleic, hydroxymaleic or pyruvic acid, phenylacetic, benzoic, p-aminobenzoic, anthranilic, p-hydroxybenzoic, salicylic or p-aminosalicylic acid, embonic acid, methanesulphonic, ethanesulphonic, hydroxyethanesulphonic, ethylenesulphonic acids, halogenbenzenesulphonic, toluenesulphonic, naphthylsulphonic acids or sulphanilic acid, methionine, tryptophane, lysine or arginine.

These or other salts of the new compounds such as e.g. picrates may serve as purifying agents of the free bases obtained as the free bases are transformed into salts, these are separated and the bases are then set free from the salts again. According to the close relationship between the new compounds in free form and in the form of their salts it will be understood from the disclosure that, if possible, the corresponding salts may be used as well as the free compounds.

The invention also relates to any embodiment of the process in which one starts from any compound obtained as an intermediate in any process step and one carries out the missing process step, or one breaks off the process at any step, or in which one forms a starting material under the reaction conditions, or in which a reaction component, possibly in the form of its salt, is present.

Thus, one may react an aldehyde or the formula XIX

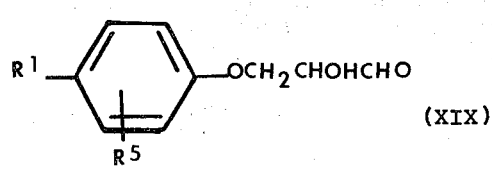

wherein R¹ and R⁵ have the same meaning as given above, with an amine of the formula

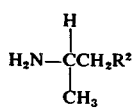

wherein R₂ has the meaning given above, in the presence of a suitable reducing agent, such as one of the above-mentioned. Thereby a compound of formula VIII is obtained as an intermediate, which then is reduced according to the description.

Further, one may in a manner known per se react an amine of the formula IV with an aldehyde or a ketone of the formula

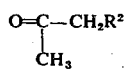

wherein R² has the above meaning, in the presence of a suitable reducing agent, such as one of the above-mentioned. Thereby, a compound of formula IX or X is obtained as an intermediate, which then is reduced according to the description.

Further, one may in a manner known per se react a phenol of formula V above with an azetidinol of the formula XX

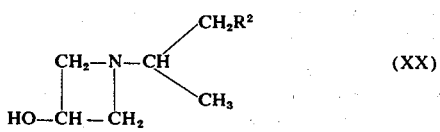

wherein R² has the meaning give above, to form a compound of formula I.

This reaction is carried out in a known way. Thus, the reaction is carried out under alkaline conditions in a suitable solvent, such as benzylalcohol by boiling the reaction mixture for some hours. Thereby the phenol is primarily converted to its metal phenolate such as alkalimetal phenolate before it is added to the azetidinol of formula XX.

The new compounds may, depending on the choice of starting materials and process, be present as optical antipodes or racemate, or if they contain at least two asymmetric carbon atoms, be present as an isomer mixture (racemate mixture).

The isomer mixtures (racemate mixtures) obtained may, depending on physical-chemical differences of the components, be separated into both stereoisomeric (diastereomeric) pure racemates, e.g. by means of chromatography and/or fractionated crystallization.

The racemates obtained can be separated according to known methods, e.g. by means of recrystallization from an optically active solvent, by means of microorganisms, or by a reaction with optically active acids forming salts of the compound and separating the salts thus obtained, e.g. by means of their different solubility in the diastereomers, from which the antipodes by the influence of a suitable agent may be set free. Suitably useable optically active acids are e.g. the L- and D-forms of tartaric acid, di-o-tolyltartaric acid, malic acid, mandelic acid, camphersulphonic acid or china acid. Preferably, the more active part of the two antipodes is isolated.

Suitably such starting materials are used for carrying out the reactions of the invention, which materials lead to groups of end products primarily especially desired and especially to the specifically described and preferred end products.

The starting materials are known or may, if they should be new, be obtained according to processes known per se.

In clinical use the compounds of the invention are administered normally orally, rectally or by injection in the form of a pharmaceutical preparation, which contains an active component either as free base or as pharmaceutically acceptable, non-toxic acid addition salt, as e.g. the hydrochloride lactate, acetate, sulphamate or the like in combination with a pharmaceutically acceptable carrier. Herein where the new compounds of the invention are mentioned either the free amine base or the acid addition salts of the free base are intended, even if the compounds are generally or specifically described, provided that the context in which such expressions are used, e.g. in the examples, permits.

The carrier may be a solid, semisolid or liquid diluent or a capsule. These pharmaceutical preparations are a further object of the invention. Usually the amount of active compound is between 0.1 and 95% by weight of the preparation, suitably between 0.5 and 20% by weight in preparations for injection and between 2 and 50% by weight in preparations for oral administration.

In the preparation of pharmaceutical preparations containing a compound of the present invention in the form of dosage units for oral administration the compound elected may be mixed with a solid, pulverulent carrier, as e.g. with lactose, saccharose, sorbitol, mannitol, starch, as potato starch, corn starch amylopectin, cellulose derivatives or gelatine, as well as with an antifriction agent such as magnesium stearate, calcium stearate, polyethyleneglycol waxes or the like, and be pressed into tablets. If coated tablets are wanted, the above prepared core may be coated with concentrated solution of sugar, which solution may contain e.g. gum arabic gelatine, talc, titaniumdioxide or the like. Furthermore, the tablets may be coated with a lacquer dissolved in an easily volatile organic solvent or mixture of solvents. To this coating a dye may be added in order to easily distinguish between tablets with different active compounds or with different amounts of the active compound present.

In the preparation of soft gelatine capsules (pearlshaped, closed capsules), which consist of gelatine, and e.g. glycerine or in the preparation of similar closed capsules the active compound is mixed with a vegetable oil. Hard gelatine capsules may contain granules of the active compound in combination with a solid, pulverulent carrier such as lactose, saccharose, sorbitol, mannitol, starch (such as e.g. potato starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil.

Liquid preparations for oral administration may be present in the form of syrups or suspensions, e.g. solutions containing from about 0.2% by weight to about 20% by weight of the active substance described, whereby the residue consists of sugar and a mixture of ethanol, water, glycerol and propylene glycol. If desired, such liquid preparations may contain coloring agents, flavoring agents, saccharine and carboxymethylcellulose as a thickening agent.

Solutions for parenteral administration by injection may be prepared as an aqueous solution of a water soluble pharmaceutically acceptable salt of the active compound, preferably in a concentration from about 0.5% by weight to about 0.10% by weight. These solutions may also contain stabilizing agents and/or buffering agents and may suitably be available in different dosage unit ampoules.

The preparation of pharmaceutical tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed during continuous and constant mixing with the binding agent solution and are moistened so that the solution is uniformly divided in the mass without overmoistening any parts. The amount of solvent is usually so adapted that the mass obtains a consistency similar to wet snow. The moistening of the pulverulent mixture with the binding agent solution causes the particles to gather together slightly in to aggregate and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully as the moisture content of the granulate is of utmost importance for the following process and for the quality of the tablets. Drying in a fluid bed may possibly be used. In this case the mass is not put on a tray but is poured into a container having a net bottom.

After the drying step the granules are sieved so that the desired particle size is obtained. Under certain circumstances powder has to be removed.

To the so-called final mixture, disintegrating, lubricants and antiadhesive agents are added. After this mixture is made the mass should have its correct composition for the tabletting step.

The cleaned tablet punching machine is provided with a certain set of punches and dies, whereupon the suitable adjustment for the weight of the tablets and the degree of compression is tested out. The weight of the tablet is decisive for the size of the dose in each tablet and is calculated starting from the amount of therapeutic agent in the granules. The degree of compression affects the size of the tablet, its strength and its ability of disintegrate in water. Especially as regards the two later properties the choice of compression pressure (0.5 to 5 ton) requires something of a balancing of properties. When the right adjustment is set, the preparation of tablets is started, which is carried out at a rate of 20,000 to 200,00 tablets per hour. The pressing of the tablets requires different times and depends on the size of the batch.

The tablets are freed from adhering powder in a specific apparatus and are then stored in closed packages until they are delivered.

Many tablets, especially those which are rough or bitter, are coated with a coating, e.g., a layer of sugar or some other suitable coating.

The tablets are usually packed by machines having an electronic counting device. The different types of packages consist of glass or plastic gallipots, but also boxes, tubes and specific dosage adapted packages may be used.

The daily dose of the active substance varies and is dependent on the type of administration, but as a general rule it is 100 to 400 mg/day of active substance in peroral administration and 5 to 20 mg per day for intravenous administration.

The following illustrates the principle and the adaptation of the invention without, however, being limited thereto. Temperatures are given in degrees Centigrade.

EXAMPLE 1

1,2-Epoxy-3-[4'-(2-acetamidoethyl)-phenoxy]-propane (2.33 g) was mixed with 25 ml of isopropanol and 1.0 g of 2-carbamoyl-1-methylethylamine. The mixture was then refluxed on a boiling water bath for 1.5 hours. Thereupon the reaction mixture was evaporated to dryness, whereby 1-(2-carbamoyl-1-methylethyl)amino-3-[4'-(2-acetamidoethyl)-phenoxy]-propanol-2 was obtained as an oil. The structure was determined using NMR.

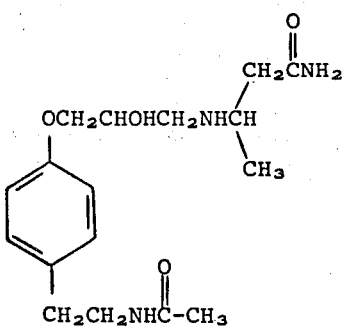

EXAMPLE 2

1,2-Epoxy-3-[4'-(2-methoxyethoxy)-phenoxy]-propane (6, 7 g) was mixed with 50 ml of isopropanol and 3,5 g of 2-(N-methyl)carbamoyl-1-methylethylamine. The mixture was refluxed on a boiling water bath for 3 hours. After evaporation to dryness 10.5 g of 1-[2-(N-methyl)-carbamoyl-methylethyl]-amino-3-[4'-(2-methoxyethoxy)-phenoxy]-propanol-2 were obtained as a yellow oil. The structure was determined using NMR

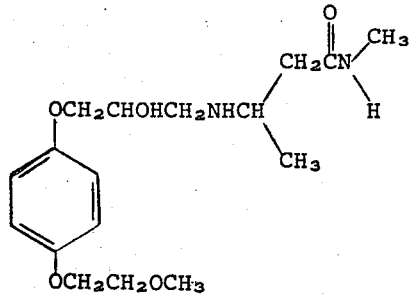

EXAMPLE 3

6.7 g of 1,2-epoxy-3-[4'-(2-methylthioethyl)phenoxy]-propane and 2.5 g of 2-cyano-1-methylethylamine were mixed with 50 ml isopropanol and the mixture was refluxed on a water bath with boiling water for 3 hours. After evaporation 9.3 g of 1-(2-cyano-1-methylethyl)amino-3-[4'-(2-methylthioethyl)phenoxy]-propanol-2 were obtained as an oil. The structure was determined using NMR

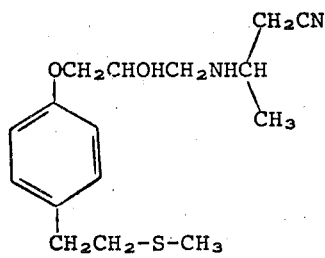

EXAMPLE 4

To a refluxing solution of 20 g of 1-methyl-3-phenylpropylamine in 100 ml of isopropanol a solution of 28.3 g of p-(2,3-epoxypropoxy)-(N-methoxycarbonyl)-phenylethylamine was added dropwise (about 15 minutes). The solution was refluxed for another 3 hours. After evaporation of the isopropanol it remained 35 g of an orange colored oil, which crystallized partly. The crystals were soaked off and dissolved in methanol, containing the calculated amount of hydrochloric acid. After recrystallization from butanone, there was recovered 7.4 g of p-[2-hydroxy-3-(1-methyl-3-phenylpropylamino)-propoxy]-(N-methoxycarbonyl)-phenethylaminehydrochloride having a melting point of 136°–139°C and the formula

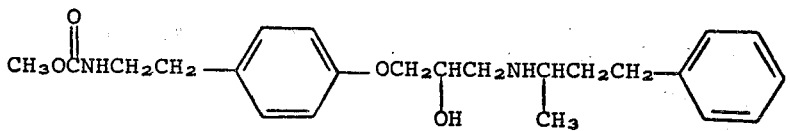

EXAMPLE 5

β-Aminobutyramide hydrochloride (12 g) was added to 150 ml of iospropanol. 3.5 g of NaOH were added and the mixture was refluxed for 1 hour. Thereupon 9 g of 1,2-epoxy-3-[4-(2-methoxyethoxy)-phenoxy]-propane were added and this mixture was refluxed for 5 h. The mixture was evaporated in vacuo and the residue was slurried in 100 ml of water, acidified with 2N HCl and shaked with ether. The aqueous phase was made alkaline with 2N NaOH and was extracted with methylene chloride. The methylene chloride phase was dried over $MgSO_4$, filtered and evaporated. The base was dissolved in isopropanol and the hydrochloride thereof was precipitated by means of gaseous HCl. The melting point of the product, 1-(1-methyl-2-carbamoylethyl)amino-3-[4-(2-methoxyethoxy)-phenoxy]-propanol-2 is 162°C (as hydrochloride). The structure was determined using NMR.

EXAMPLE 6

1-(2-(N-methyl)-carbamoyl-1-methylethyl)-amino-3-[4-(2-acetamidoethyl)-phenoxy]-propanol-2 was prepared from 1,2-epoxy-3-[4-(2-acetamidoethyl)-phenoxy]-propane and 2-(N-methyl)-carbamoyl-1-methyethylamine in accordance with Example 1 above. The substance as a base is an oil. The structure was determined using NMR.

EXAMPLE 7 (Method B)

10 g of 4-(2-methoxyethoxy)-phenylglycidylether in 100 ml of ethanol were saturated with gaseous ammonia and the mixture was heated in an autoclave on a boiling water bath for 4 hours. The solvent was evaporated and the residue was dissolved in ethylacetate and HCl-gas was introduced. The hydrochloride then precipitated and it was filtered off and dissolved in 50 ml of ethanol to which 2-cyano-1-methylethylamine and 15 g of $K_2CO_3$ had been added. The mixture was heated in an autoclave at 130°C for 10 hours whereupon the solvent was evaporated and the residue was mixed with 100 ml of 2N HCl and 100 ml of ether. The aqueous phase was separated off and was made alkaline with 2N NaOH and extracted with ethyl acetate. The solvent phase was dried over $K_2CO_3$, whereupon 1-(1-methyl-2-cyano-ethyl)amino-3-[4-(2-methoxyethoxy)-phenoxy]-propanol-2 was obtained as an oil.

EXAMPLE 8 (Method C)

2.4 g of Na were dissolved in 100 ml of ethanol, whereupon 15.2 g of 4-(2-methoxyethoxy)phenol and 17.6 g of 1-(1-methyl-2-cyanoethyl)amino-3-chloropropanol-2 were added. The mixture was heated in a autoclave on a boiling water bath for 15 hours. Thereupon it was filtered and the filtrate was evaporated to dryness. The residue was made acidic with 2N HCl and extracted with ether, whereupon the aqueous phase was made alkaline with 2N NaOH and extracted with ethylacetate. The ethylacetate was dried over $MgSO_4$ and 1-(1-methyl-2-cyanoethyl) amino-3-[4-(2-methoxyethoxy)-phenoxy]-propanol-2 was obtained as an oil.

EXAMPLE 9 (Method D)

In accordance with Example 8 above N-benzyl-1-(1-methyl-2-cyanoethyl)amino-3-[4-(2-methoxyethoxy)-phenoxy]-propanol-2 was prepared from 4-(2-methoxyethoxy)phenol and N-benzyl-1-(1-methyl-2-cyanoethyl)amino-3-chloropropanol-2 p-hydroxybenzoate, 10 g of the compound thus obtained were dissolved in 100 ml of ethanol, 0.5 g of Pd/C (10%) catalyst were added and hydrogenation was carried out until the estimated amount of $H_2$ had been absorbed. After filtration the mixture was evaporated to dryness and the residue 1-(1-methyl-2-cyanoethyl)amino13-[4-(2-methoxyethoxy)phenoxy]-propanol-2 was obtained as an oil.

EXAMPLE 10 (Method E)

10 g of 1-amino-3-[4-(2-methoxyethoxy)phenoxy]-propanol-2 prepared in accordance with Example 5 above were dissolved in 80 ml of methanol containing 5 g of cyanoacetone. The solution was cooled on an ice bath and 10 g of sodium borohydride was added little by little. The temperature was allowed to rise to room temperature and after 1 hour 200 ml of $H_2O$ were added and the mixture was extracted with ethylacetate. The ethylacetate phase was dried over $K_2CO_3$ and the compound 1-(1-methyl-2-cyanoethyl)amino-3-[4-(2- methoxyethoxy)phenoxy]-propanol-2 was obtained as an oil.

EXAMPLE 11 (Method F)

10 g of 1-(1-methyl-2-(N-methylcarbamoyl)amino-3-[4-hydroxyphenoxy]-propanol-2, 10 g of 2-chloroethylmethylether and 15 g of $K_2CO_3$ were mixed in 100 ml of acetonitrile and were refluxed for 5 hours during stirring. Filtration and evaporation gave 1-(1-methyl-2-N-methylcarbamoylethyl)amino-3-[4-(2-methoxyethoxy)phenoxy]-propanol-2 as an oil. The structure was determined using NMR.

EXAMPLE 12 (Method G)

11.6 g of 4-(methoxyethoxy)phenol, 8.0 g of 1-(methyl-2-cyanoethyl)-3-acetidinol, 50 g of benzylalcohol and 0.3 g of KOH was heated to 140°C for 6 hours while stirring. After cooling the mixture was extracted with 2N HCl. The aqueous phase was made alkaline and the compound was extracted with chloroform. The chloroform phase was dried and evaporated. 1-(1-methyl-2-cyanoethyl)amino-3-[4-(2-methoxyethoxy)phenoxy]-propanol-2 was obtained as an oil.

EXAMPLE 13

A syrup containing 2% (weight per volume) of active substance was prepared from the following ingredients:

| | |
|---|---|
| 1-(2-carbamoyl-1-methylethyl)amino-3-[4'-(2-acetamidoethyl)-phenoxy]-propanol-2.HCl | 2.0 g |
| Saccharine | 0.6 g |
| Sugar | 30.0 g |
| Glycerine | 5.0 g |
| Flavoring agent | 0.1 g |
| Ethanol 96% | 10.0 ml |
| Distilled water ad | 100.0 ml |

Sugar, saccharine and the ether salt were dissolved in 60 g of warm water. After cooling glycerine and a solution of flavoring agents dissolved in ethanol were added. To the mixture water was then added to 100 ml.

The above-named active substance may be replaced with other pharmaceutically acceptable acid addition salts.

EXAMPLE 14

1-[2-(N-methyl)-carbamoyl-1-methylethyl]amino-3-[4'-(2-methoxyethoxy)-phenoxy]-propanol-2 hydrochloride (250 g) was mixed with lactose (175.8 g), potato starch (169.7 g) and colloidal silicic acid (32 g). The mixture was moistened with a 10% solution of gelatine and was granulated through a 12 mesh sieve. After drying potato starch (160 g), talc (50 g) and magnesium stearate (5 g) were admixed and the mixture thus obtained was pressed into tablets (10 000) which contain 25 mg of substance. The tablets are sold on the market provided with a breaking score to give another dose than 25 mg or to give multiples thereof when broken.

EXAMPLE 15

Granules were prepared from 1-(2-cyano-1-methylethyl)amino-3-[4'-(2-methylthioethyl)-phenoxy]-propanol-2 hydrochloride (250 g), lactose (175.9 g) and an alcoholic solution of polyvinylpyrrolidone (25 g). After the drying step the granules were mixed with talc (25 g) potato starch (40 g) and magnesium stearate (2.50 g) and was pressed into 10 000 biconvex tablets. These tablets are primarily coated with a 10% alcoholic solution of shellac and thereupon with an aqueous solution containing saccharose (45%), gum arabicum (5%), gelatine (4%) and dyestuff (0.2%). Talc and powdered sugar were used for powdering after the first five coatings. The coating was then coated with a 66% sugar syrup and polished with a 10% carnauba wax solution in carbon tetrachloride.

EXAMPLE 16

1-(2-benzyl-1-methylethyl)amino-3-[4'-(2-(N-methoxycarbonyl)-aminoethyl)-phenoxy]-propanol-2-hydrochloride (1 g), sodiumchloride (0.8 g) and ascorbic acid (0.1 g) were dissolved in sufficient amount of distilled water to give 100 ml of solution. This solution, which contains 10 mg of active substance on each ml, was used in filling ampoules, which were sterilized by heating at 120°C for 20 minutes.

We claim:
1. A method for blocking adrenergic β-receptor stimulation in the treatment of cardiovascular diseases, comprising administering to a mammal in which a β-receptor blockade is desired an amount, effective to provide antagonism to adrenergic β-receptor stimulation, of a compound of formula I

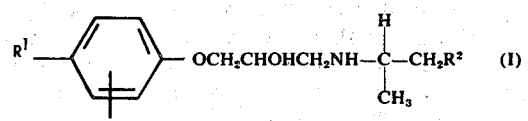

wherein $R^1$ is a loweralkylthio loweralkyl, loweralkoxy loweralkoxy, $R^2$ is a group

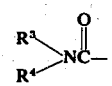

wherein $R^3$ and $R^4$ are hydrogen or loweralkyl and $R^5$ is hydrogen, halogen, loweralkyl, loweralkenyl, loweralkinyl, loweralkoxy-methyl, loweralkoxy, loweralkenyloxy or loweralkinyloxy or its therapeutically acceptable acid addition salt.

2. A method according to claim 1 wherein said compound has the formula Ia

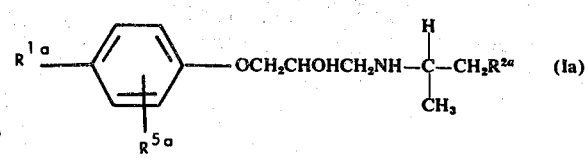

wherein $R^{1a}$ is a loweralkylthio loweralkyl, $R^{2a}$ is carbamoyl, loweralkylcarbamoyl or diloweralkylcarbamoyl and $R^{5a}$ is hydrogen, halogen, loweralkyl, loweralkenyl, loweralkoxy-methyl, loweralkoxy or loweralkenyloxy.

3. A method according to claim 1 wherein $R^{1a}$ is loweralkylthioloweralkyl, $R^{2a}$ is carbamoyl, loweralkylcarbamoyl or diloweralkylcarbamoyl, and $R^{5a}$ is hydrogen, chloro, bromo, methyl, allyl, methoxymethyl, methoxy or allyloxy.

4. A method according to claim 1 wherein $R^{1a}$ is 2-methylthioethyl, $R^{2a}$ is carbamoyl or methylcarbamoyl, and $R^{5a}$ is hydrogen.

5. A method according to claim 1 wherein said compound has a formula Ib

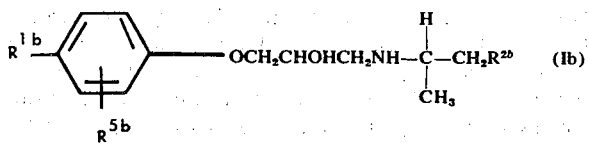

wherein $R^{1b}$ is loweralkoxy loweralkoxy, $R^{2b}$ is carbamoyl, loweralkylcarbamoyl or diloweralkylcarbamoyl and $R^{5b}$ is hydrogen, halogen, loweralkyl, loweralkenyl, loweralkoxymethyl, loweralkoxy or loweralkenyloxy.

6. A method according to claim 5 wherein $R^{1b}$ is 2-ethoxyethoxy, 2-methoxyethoxy or 3-methoxy-n-propoxy, $R^{2b}$ is carbamoyl, methylcarbamoyl or dimethylcarbamoyl, and $R^{5b}$ is hydrogen, chloro, bromo, methyl, allyl, methoxymethyl, methoxy or allyloxy.

7. A method according to claim 5 wherein $R^{1b}$ is 2-methoxyethoxy, $R^{2b}$ is carbamoyl or N-methylcarbamoyl and $R^{5b}$ is hydrogen.

8. A method according to claim 1 wherein said compound is in the form of a dextro-rotating optical antipode.

9. A method according to claim 1 wherein said compound is in the form of its levo-rotating optical antipode.

10. A method according to claim 1 wherein said compound is in a free base form.

11. A method according to claim 1 wherein said compound is in the form of a therapeutically acceptable acid addition salt.

12. A method according to claim 1 wherein said compound is 1-[4-(2-methoxyethoxy)-phenoxy]-2-hydroxy-3-[2-(N-methyl)-carbamoyl-1-methylethyl]-aminopropane.

13. A method according to claim 1 wherein said compound if 1-[4-(2-methoxyethoxy-phenoxy]-2-hydroxy-3-(1-methyl-2-carbamoylethyl)-aminopropane.

14. A pharmaceutical composition useful for blocking adrenergic B-receptor stimulation in the treatment of cardiovascular diseases containing a compound of formula I

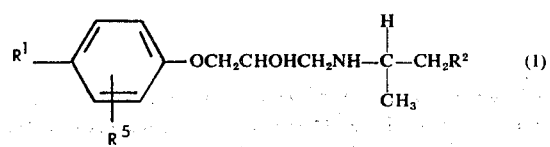

wherein $R^1$ is a loweralkylthio loweralkyl, loweralkoxy loweralkoxy, $R^2$ is a group

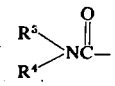

wherein $R^3$ and $R^4$ are hydrogen or loweralkyl and $R^5$ is hydrogen, halogen, loweralkyl, loweralkenyl, loweralkinyl, loweralkoxy-methyl, loweralkoxy, loweralkenyloxy or loweralkinyloxy or its therapeutically acceptable acid addition salt and a therapeutically acceptable carrier therefor, said composition containing from 0.1 to 95% by weight of said compound I.

15. A pharmaceutical composition according to claim 14 in a form suitable for administration by injection wherein said compound I comprises about 0.5 to about 20% by weight of said composition.

16. A pharmaceutical composition according to claim 14 in a form suitable for oral administration wherein said compound I comprises about 2% to about 50% by weight of said composition.

17. A pharmaceutical composition according to claim 14 wherein said compound has the formula Ia

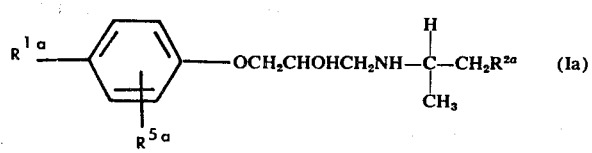

wherein $R^{1a}$ is a loweralkylthio loweralkyl, $R^{2a}$ is carbamoyl, loweralkylcarbamoyl or diloweralkylcarbamoyl and $R^{5a}$ is hydrogen, halogen, loweralkyl, loweralkenyl, loweralkoxy-methyl, loweralkoxy or loweralkenyloxy.

18. A pharmaceutical composition according to claim 11 wherein $R^{1a}$ is loweralkylthioloweralkyl, $R^{2a}$ is carbamoyl, loweralkylcarbamoyl or diloweralkylcarbamoyl, and $R^{5a}$ is hydrogen, chloro, bromo, methyl, allyl, methoxymethyl, methoxy or allyloxy.

19. A pharmaceutical composition according to claim 17 wherein $R^{1a}$ is 2-methylthioethyl, $R^{2a}$ is carbamoyl or methylcarbamoyl, and $R^{5a}$ is hydrogen.

20. A pharmaceutical composition according to claim 14 wherein said compound has the formula Ib

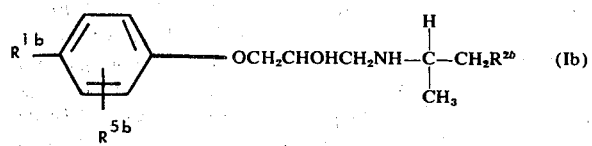

wherein $R^{1b}$ is loweralkoxy loweralkoxy, $R^{2b}$ is carbamoyl, loweralkylcarbamoyl or diloweralkylcarbamoyl and $R^{5b}$ is hydrogen, halogen, loweralkyl, loweralkenyl, loweralkoxy-methyl, loweralkoxy or loweralkenyloxy.

21. A pharmaceutical composition according to claim 20 wherein $R^{1b}$ is 2-ethoxyethoxy, 2-methoxyethoxy or 3-methoxy-n-propoxy, $R^{2b}$ is carbamoyl, methylcarbamoyl or dimethylcarbamoyl, and $R^{5b}$ is hydrogen, chloro, bromo, methyl, allyl, methoxymethyl, methoxy or allyloxy.

22. A pharmaceutical composition according to claim 20 wherein $R^{1b}$ is 2-methoxyethoxy, $R^{2b}$ is carbamoyl or N-methylcarbamoyl and $R^{5b}$ is hydrogen.

23. A pharmaceutical composition according to claim 14 wherein said compound is in the form of a dextro-rotating optical antipode.

24. A pharmaceutical composition according to claim 14 wherein said compound is in the form of its levo-rotating optical antipode.

25. A pharmaceutical composition according to claim 14 wherein said compound is in a free base form.

26. A pharmaceutical composition according to claim 14 wherein said compound is in the form of a therapeutically acceptable acid addition salt.

27. A pharmaceutical composition according to claim 14 wherein said compound is 1-[4-(2-methoxyethoxy)-phenoxy]-2-hydroxy-3-[2-(N-methyl)-carbamoyl-1-methylethyl]-aminopropane.

28. A pharmaceutical composition according to claim 14 wherein said compound is 1-[4-(2-methoxyethoxy)-phenoxy]-2-hydroxy-3-(1-methyl-2-carbamoylethyl)-aminopropane.

* * * * *

UNITED STATES PATENT AND TRADEMARK OFFICE
CERTIFICATE OF CORRECTION

PATENT NO. : 3,949,088

DATED : April 6, 1976

INVENTOR(S) : Benny R. Samuelsson et al.

It is certified that error appears in the above-identified patent and that said Letters Patent are hereby corrected as shown below:

Col. 24, Line 41, "claim 11" should be --claim 17--.

Signed and Sealed this

Twelfth Day of April 1977

[SEAL]

Attest:

RUTH C. MASON
*Attesting Officer*

C. MARSHALL DANN
*Commissioner of Patents and Trademarks*